United States Patent [19]

Ohtsubo et al.

[11] Patent Number: 4,760,084
[45] Date of Patent: Jul. 26, 1988

[54] DRY PESTICIDAL COMPOSITIONS

[75] Inventors: Toshiro Ohtsubo; Shigeru Maruyama, both of Toyonaka; Takashi Tamura, Yokohama; Nobuyuki Hirano, Toyonaka; Masami Sakai, Kakogawa, all of Japan

[73] Assignee: Sumitomo Chemical Company, Limited, Osaka, Japan

[21] Appl. No.: 887,783

[22] Filed: Jul. 21, 1986

[30] Foreign Application Priority Data

Jul. 29, 1985 [JP] Japan .................. 60-167973

[51] Int. Cl.⁴ ..................... A01N 37/34; A01N 53/00
[52] U.S. Cl. .................... 514/521; 514/531; 514/951; 514/952
[58] Field of Search ............... 514/765, 531, 521, 951, 514/952; 424/406, 409

[56] References Cited

U.S. PATENT DOCUMENTS 3,755,582  8/1973  Bullock ............... 424/251

FOREIGN PATENT DOCUMENTS

| 3343092 | 6/1985 | Fed. Rep. of Germany ...... 514/521 |
| 1573875 | 7/1969 | France . |
| 58-57301 | 4/1983 | Japan . |
| 0243001A | 5/1984 | Japan . |

OTHER PUBLICATIONS

Windholz et al., The Merck Index, 1983, Nos. 2763, 3921, 3933, 6936 and 7041.
Chemical Patents Index, Basic Abstracts Journal, Sec. C, Week 8603, 3/1986, Abstract No. 18497.

Primary Examiner—Albert T. Meyers
Assistant Examiner—Richard Kearse
Attorney, Agent, or Firm—Stevens, Davis, Miller & Mosher

[57] ABSTRACT

A dry pesticidal composition of a toxicant having a melting point in a range of from 0° C. to 65° C. (the said range of melting point applies also to the melting point of a mixture of toxicants) containing a hydrocarbon represented by the formula,

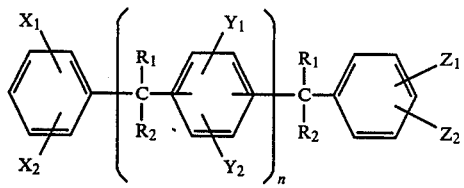

wherein $X_1$, $X_2$, $Y_1$, $Y_2$, $Z_1$ and $Z_2$, which may be the same or different represent a hydrogen atom or an alkyl group having 2 or less carbon atom, $R_1$ and $R_2$, which may be the same or different, represent a hydrogen atom or a methyl group, and n represents 0 or 1.

10 Claims, No Drawings

DRY PESTICIDAL COMPOSITIONS

Present invention relates to dry pesticidal compositions of a toxicant having a melting point in a range of from 0° C. to 65° C. (the said range of melting point applies also to the melting point of a mixture of toxicants) containing a hydrocarbon represented by the formula (1) (hereinafter referred to as present compound),

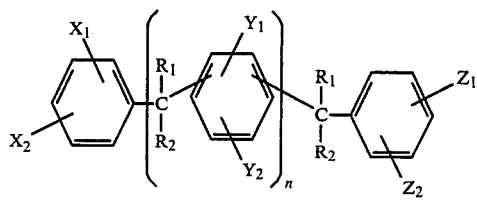

(1)

wherein $X_1$, $X_2$, $Y_1$, $Y_2$, $Z_1$ and $Z_2$, which may be the same or different, represent a hydrogen atom or an alkyl group having 2 or less carbon atom, $R_1$ and $R_2$, which may be the same or different, represent a hydrogen atom or a methyl group, and n represents 0 or 1.

The effect of pesticides is developed in amounts of, generally, several ten grams to several hundred grams per hectare of active ingredients contained therein. Since, however, it is very difficult to scatter uniformly a toxicant alone at such a low dosage level as above over a wide range, it is a common practice to dilute the toxicant with a proper diluent so that the toxicant can easily be scattered. Chemicals thus produced are pesticidal compositions, of which the greatest object is to change the toxicant into easily usable forms. Also, it may be said that another great object of the pesticidal compositions is to develop the effect of the toxicant to a maximum, and when the toxicant has defects, to cover the defects to make the toxicant problem-free pesticides.

One form of such pesticidal compositions is dry pesticidal compositions, which are obtained in a solid form. Representative examples of dry pesticidal compositions include wettable powders, granules, dusts, etc.

Any of the dry pesticidal compositions is produced by diluting toxicants with a solid. Explanation will be given below in more detail.

Wettable powders are finely powdered compositions produced by pulverizing and mixing toxicants together with surface active agents in small amounts and finely powdered carriers. When they are used, they are diluted with water into a suspension, and applied by means of a sprayer.

Consequently, the particularly important physical properties of wettable powders are suspensibility, fineness and wettability. These physical properties should be maintained even after long-term storage like the stability of active ingredients in the pesticidal compositions.

Dusts are preparations produced by diluting toxicants with finely powdered carriers and different from wettable powders in that they are applied as such by means of dusting machines without dilution with water at the time of use. For this purpose, it is required that the fineness dost not reduce and the dispersibility is kept good even after long-term storage, and therefore caking of the powders during storage is not preferred.

Granules are mainly produced by methods such as kneading-extrusion-granulation, impregnation, coating, etc., and take a granular form in any of them. Granules are more frequently applied to water surface or soil than directly applied to target crops. After application to water surface or soil, the active ingredient of granules dissolves in water or vaporizes to reach its action sites and displays the effect. It is therefore required that the same proper water-disintegrability and vaporizability as those at the time of formulation are maintained even after long-term storage.

Hitherto, in formulating toxicants having a melting point in a range of from 0° C. to 65° C. into these dry compositions, there are two cases wherein the toxicants are handled, on the one hand, as solid and, on the other hand, as liquid. In the former case, a great care should be given to the fusion of toxicants at steps accompanied by generation of heat such as a pulverization step, etc. and the formation of agglomeration caused by the fusion. In the latter case, there are various problems such as a need of the installation of heating apparatus for the complete dissolution of toxicants, etc. As described above, in order to obtain dry pesticidal compositions of good initial physical property, there was a need to control sufficiently the manufacturing process as compared with cases wherein toxicants having a melting point exceeding 65° C. or not exceeding 0° C. are formulated into dry compositions. In addition, even if dry pesticidal compositions with good initial physical property are obtained, there is a possibility that toxicants take a liquid and solid forms alternately depending upon the condition of long-term storage, thereby resulting in the deterioration of the physical property. For example, the deterioration of the physical property sometimes appears in the form of reduction in the suspensibility and fineness for wettable powders, caking of powders during storage for dusts, wettable powders and granules and change in the amount of active ingredients released after application for granules.

The present inventors extensively studied to make it easier to prepare the dry pesticidal compositions of such toxicants having a melting point in a range of from 0° C. to 65° C., and besides to cause the dry pesticidal compositions to hold satisfactory physical properties even after long-term storage, and as a result, found that dry pesticidal compositions meeting the above objects can be obtained by adding the present hydrocarbon to the compositions.

The present hydrocarbon has also advantages that it has little irritating odor and a high flash point so that handling is easy, and also that there is no need for special deodorizing or local ventilating equipments, etc. at the time of use. Further, the present inventors confirmed that phytotoxicity to crops is little even if the present hydrocarbon is added to the compositions, and besides that compositions having no dangers of reduction in physical property, ignition, explosion, etc. owing to the vaporization of offensive solvents can be obtained. The present inventors thus completed the present invention.

Specific examples of the present hydrocarbon and the toxicant having a melting point in a range of from 0° C. to 65° C. are shown in Tables 1 and 2, respectively, but it is a matter of course that both the hydrocarbon and the compound are not limited to these examples. Also, both the hydrocarbon and the compound sometimes have respective isomers, but these isomers are also of course included in the scope of the present invention.

TABLE 1

| Hydrocarbon | Name of compound |
| --- | --- |
| (1) | 1,1-Diphenylethane |
| (2) | 1,1-Ditolylethane |
| (3) | 1-Phenyl-1-xylylethane |
| (4) | 1-Phenyl-1-(ethylphenyl)ethane |
| (5) | 1-Xylyl-1-(α-methylbenzylphenyl)ethane |
| (6) | Bis(α-methylbenzyl)xylene |

TABLE 2

| Toxicant | Name of compound |
| --- | --- |
| (a) | 2-sec-Butylphenyl N—methylcarbamate |
| (b) | α-Cyano-3-phenoxybenzyl 3-(2,2-dichlorovinyl)-2,2-dimethylcyclopropanecarboxylate [cypermethrin] |
| (c) | 0-(3,5,6-Trichloro-2-pyridyl) 0,0-diethylphosphorothioate |
| (d) | 3-Phenoxybenzyl 3-(2,2-dichlorovinyl)-2,2-dimethylcyclopropanecarboxylate [permethrin] |
| (e) | α-Cyano-3-phenoxybenzyl 2,2,3,3-tetramethylcyclopropanecarboxylate [fenpropathrin] |
| (f) | α-Cyano-3-phenoxybenzyl 2-(4-chlorophenyl)-3-methylbutyrate [fenvalerate] |
| (g) | 3,4,5,6-Tetrahydrophthalimidomethyl chrysanthemate |
| (h) | 2-{1-Methyl-2-(4-phenoxyphenoxy)ethoxy}-pyridine |

In the practice of the present invention, the present hydrocarbons may be used alone or in mixture of two or more of them. Also, the melting point of these hydrocarbons is preferably 0° C. or less. Further, other solvents meeting the object of the present invention for their little irritating odor and high flash point, for example indane derivatives, etc. may be added at the same time. In this case, however, the amount of the solvents added at the same time is preferably 15 wt. % or less based on the present hydrocarbon.

Of the present hydrocarbons, 1-phenyl-1-xylylethane is particularly preferred because it is commercially available. As a matter of course, it is preferred to select the combination of the toxicants with the present hydrocarbons based on a good compatibility between the both.

The stability of the physical property of dry pesticidal compositions is improved according to the amount of the present hydrocarbon added. The amount varies also with the kind of the toxicant, but generally, it is preferred that the amount is 20 wt.% or more based on the toxicant, and besides that the total of the present hydrocarbon and the toxicant is 60 wt.% or less based on dry pesticidal compositions. The toxicants may of course be used alone, but they may be used as a mixture of two or more of them. In the latter case, the melting points of individual toxicants need not be taken into account, and it suffices for the mixture to have a melting point in a range of from 0° C. to 65° C.

Of the dry pesticidal compositions of the present invention, wettable powders are produced using a carrier and a surface active agent in addition to the present hydrocarbon and the toxicant. As the carrier, preferred one or more are used which are selected from the group consisting of fine powders of minerals such as diatomaceous earth, calcium carbonate, talc, pyrophyllite, kaolinite, montmorillonite, attapulgite, bentonite, etc., fine powders of synthetic compounds such as synthetic hydrated silicon dioxide, etc., and vegetable fine powders such as soybean powders, wood powders, walnut shell powders, etc. As the surface active agent, preferred one or more are used which are selected from the group consisting of anionic surface active agents such as sodium salts, calcium salts, magnesium salts or amine salts of dodecylbenzenesulfonic acid, alkylnaphthalenesulfonic acid, dialkyl sulfosuccinate, polyoxyethylene alkylaryl ethersulfuric acid ester, polyoxyethylene alkylarylphenylphosphoric acid, alkylnaphthalenesulfonic acid/formalin condensates, lignosulfonic acid, etc., and nonionic surface active agents such as polyoxyethylene alkyl ether, polyoxyethylene alkylaryl ether, polyoxyethylene fatty acid ester, polyoxyethylene sorbitan alkylate, etc. Also, water-soluble polymers such as polyvinyl alcohol, carboxymethyl cellulose, etc. may be used in place of these surface active agents. Further, auxiliaries commonly used in formulation by those skilled in the art such as synergists, stabilizers, antioxidants, etc. may optionally be used if necessary.

Of the dry pesticidal compositions of the present invention, dusts are produced using common carriers for dusts in addition to the present hydrocarbon and the toxicant. As the carrier, preferred one or more are used which are selected from the group consisting of fine powders of minerals such as diatomaceous earth, calcium carbonate, talc, pyrophyllite, kaolinite, montmorillonite, attapulgite, vermiculite, etc., fine powders of synthetic compounds such as synthetic hydrated silicon dioxide, etc., and vegetable fine powders such as soybean powders, wood powders, walnut shell powders, etc. Also, auxiliaries commonly used in formulation by those skilled in the art such as synergists, stabilizers, antioxidants, etc. may optionally be used if necessary.

Of the dry pesticidal compositions of the present invention, granules are produced using common carriers for granules in addition to the present hydrocarbon and the toxicant. As the carrier, preferred one or more are used which are selected from the foregoing same mineral, synthetic and vegetable carriers as used in preparation of dusts. The fineness of carrier powders depends upon the granule manufacturing methods such as kneading-extrusion-granulation, coating, impregnation, etc., so that it is selected so as to meet the respective methods.

In the preparation of granules, surface active agents are preferably used in general, and the same ones as used in the preparation of wettable powders described above may be given. Also, in the same manner as described above, water-soluble polymers such as polyvinyl alcohol, carboxymethyl cellulose, etc. may be used in place of the surface active agents. Further, auxiliaries commonly used in formulation by those skilled in the art such as synergists, stabilizers, antioxidants, etc. may optionally be used if necessary.

For producing the dry pesticidal compositions of the present invention, it is a common practice to mix the toxicant having a melting point in a range of from 0° C. to 65° C. with the present hydrocarbon into a uniform solution and then mix the resulting solution with the carriers and if necessary the surface active agents or water-soluble polymers or/and auxiliaries.

The present invention will be illustrated in more detail with reference to the following examples, comparative examples and test examples, but it is not of course limited to these examples.

EXAMPLE 1

Five parts of a toxicant (b), 2.5 parts of a hydrocarbon (3) and 2.5 parts of a hydrocarbon (4) were mixed in a beaker, and to this mixture was added a mixture of 3 parts of calcium lignosulfonate, 4 parts of Sorpol 5060 (a surface active agent, produced by Toho Kagaku Kogyo Co.), 15 parts of synthetic hydrated silicon dioxide and 68 parts of diatomaceous earth. After pre-mixing, the resulting mixture was uniformly mixed on a juice mixer to obtain a good 5% wettable powder of the toxicant (b).

EXAMPLE 2

Twenty parts of toxicant (f) and 10 parts of a hydrocarbon (3) were mixed in a beaker, and to this mixture was added a mixture of 6 parts of Sorpol 5060 (the same as described above), 2 parts of calcium lignosulfonate, 30 parts of synthetic hydrated silicon dioxide and 32 parts of diatomaceous earth. The resulting mixture was treated in the same manner as in Example 1 to obtain a good 20% wettable powder of the toxicant (f).

EXAMPLE 3

Twenty parts of a toxicant (a), 6 parts of a hydrocarbon (3) and 6 parts of a hydrocarbon (4) were mixed and added dropwise to a mixture, previously mixed on a ribbon mixer, of 25 parts of synthetic hydrated silicon dioxide, 37 parts of diatomaceous earth, 2 parts of calcium lignosulfonate, 3 parts of Sorpol 2495 G (a surface active agent, produced by Toho Kagaku Kogyo Co.) and 1 part of Sorpol 5080 (a surface active agent, produced by Toho Kagaku Kogyo Co.). After pre-mixing the whole mixture, the mixture was pulverized on a centrifugal pulverizer to obtain a good 20% wettable powder of the toxicant (a).

EXAMPLE 4

Five parts of a toxicant (e), 2.5 parts of a hydrocarbon (3) and 2.5 parts of a hydrocarbon (4) were mixed in a beaker, and to this mixture was added a mixture of 3 parts of calcium lignosulfonate, 4 parts of Sorpol 5060 (the same as described above), 15 parts of synthetic hydrated silicon dioxide and 68 parts of diatomaceous earth. The resulting mixture was treated in the same manner as in Example 1 to obtain a good 5% wettable powder of the toxicant (e).

EXAMPLE 5

Ten parts of a toxicant (d), 7.5 parts of a hydrocarbon (3) and 2.5 parts of a hydrocarbon (4) were mixed in a beaker, and to this mixture was added a mixture, previously mixed in another beaker, of 15 parts of synthetic hydrated silicon dioxide, 3 parts of calcium lignosulfonate, 6 parts of Sorpol 2495 G (the same as described above) and 56 parts of diatomaceous earth. The resulting mixture was treated in the same manner as in Example 1 to obtain a good 10% wettable powder of the toxicant (d).

EXAMPLE 6

Five parts of a toxicant (b) and 5 parts of a hydrocarbon (1) were mixed in a beaker, and to this mixture was added a mixture of 3 parts of calcium lignosulfonate, 4 parts of Sorpol 5060 (the same as described above), 15 parts of synthetic hydrated silicon dioxide and 68 parts of diatomaceous earth. The resulting mixture was treated in the same manner as in Example 1 to obtain a good 5% wettable powder of the toxicant (b).

EXAMPLE 7

Procedure was carried out in the same manner as in Example 6 except that 5 parts of a toxicant (b) and 5 parts of a hydrocarbon (2) were used, to obtain a good 5% wettable powder of the toxicant (b).

EXAMPLE 8

Ten parts of a toxicant (a) and 5 parts of a hydrocarbon (3) were mixed in a beaker, and to this mixture were added 15 parts of synthetic hydrated silicon dioxide and 70 parts of clay. After pre-mixing, the resulting mixture was pulverized on a juice mixer to obtain a good 10% dust of the toxicant (a).

EXAMPLE 9

Ten parts of a toxicant (e), 2 parts of a hydrocarbon (1), 5 parts of a hydrocarbon (2), 10 parts of synthetic hydrated silicon dioxide, 35 parts of bentonite, 15 parts of diatomaceous earth, 2 parts of Sorpol 5060 (the same as described above) and 21 parts of clay were uniformly mixed, uniformly kneaded with water and granulated on a granulator to obtain a good 10% granule of the toxicant (e).

EXAMPLE 10

Ten parts of a toxicant (b) and 2 parts of a hydrocarbon (1) were mixed in a beaker, and to this mixture were added 10 parts of synthetic hydrated silicon dioxide, 35 parts of bentonite, 15 parts of diatomaceous earth, 2 parts of Sorpol 5060 (the same as described above) and 21 parts of clay. The resulting mixture was treated in the same manner as in Example 9 to obtain a good 10% granule of the toxicant (b).

EXAMPLE 11

Five parts of a toxicant (b) and 3 parts of a hydrocarbon (5) were mixed in a beaker, and to this mixture was added a mixture of 5 parts of Sorpol 5060 (the same as described above), 3 parts of calcium lignosulfonate, 15 parts of synthetic hydrated silicon dioxide and 69 parts of diatomaceous earth. The resulting mixture was treated in the same manner as in Example 1 to obtain a good 5% wettable powder of the toxicant (b).

EXAMPLE 12

Ten parts of a toxicant (f), 1 part of a toxicant (g), 7.5 parts of a hydrocarbon (3), 1.8 parts of a hydrocarbon (4) and 0.6 parts of 2-methyl-4-phenylindane were mixed in a beaker, and to this mixture was added a mixture of 6 parts of Sorpol 2495 G (the same as described above), 2 parts of calcium lignosulfonate, 20 parts of synthetic hydrated silicon dioxide and 51.1 parts of diatomaceous earth. The resulting mixture was treated in the same manner as in Example 1 to obtain a good mixed wettable powder of the toxicants (f) and (g).

COMPARATIVE EXAMPLE 1

Twenty parts of a toxicant (f) was added to a beaker, and to this beaker was added a mixture of 6 parts of Sorpol 5060 (the same as described above), 2 parts of calcium lignosulfonate, 30 parts of synthetic hydrated silicon dioxide and 42 parts of diatomaceous earth. After pre-mixing, the resulting mixture was mixed on a juice mixer to obtain a 20% wettable powder of the toxicant (f).

COMPARATIVE EXAMPLE 2

Five parts of a toxicant (e) was added to a beaker, and to this beaker was added a mixture of 3 parts of calcium lignosulfonate, 4 parts of Sorpol 5060 (the same as described above), 15 parts of synthetic hydrated silicon dioxide and 73 parts of diatomaceous earth. The resulting mixture was treated in the same manner as in Comparative Example 1 to obtain a 5% wettable powder of the toxicant (e).

COMPARTIVE EXAMPLE 3

Procedure was carried out in the same manner as in Comparative Example 2 except that 5 parts of a toxicant (b) was used, to obtain a 5% wettable powder of the toxicant (b).

COMPARATIVE EXAMPLE 4

Ten parts of a toxicant (a) was added to a beaker, and to this beaker were added 15 parts of synthetic hydrated silicon dioxide and 75 parts of clay. After pre-mixing, the resulting mixture was pulverized on a juice mixer to obtain a 10% dust of the toxicant (a).

COMPARATIVE EXAMPLE 5

Ten parts of a toxicant (e), 10 parts of white carbon, 35 parts of bentonite, 15 parts of diatomaceous earth, 2 parts of Sorpol 5060 (the same as described above) and 28 parts of clay were mixed, uniformly kneaded with water and granulated on a granulator to obtain a 10% granule of the toxicant (e).

TEST EXAMPLE 1

100 Grams of each of the wettable powders produced in Examples 2 and 4 and Comparative Examples 1 and 2 were enclosed in an aluminum bag and stored at 0° C. for 60 days. Thereafter, 50 g of each wettable powder was weighed and subjected to the wet sieving test with a 46μsieve. The residue on the sieve was transferred to a Petri dish, dried on a water bath and weighed. The content of the residue on sieve of the test sample was calculated by weight percent. The results are shown in Table 3 together with the test results on the same wettable powders as produced.

TABLE 3

| Wettable powder used for test | Residue on sieve (%) | |
|---|---|---|
| | Before storage | After 60 days' storage at 0° C. |
| Example 2 | 0.7 | 0.9 |
| Comparative Example 1 | 0.8 | 6.2 |
| Example 4 | 0.9 | 0.8 |
| Comparative Example 2 | 0.6 | 5.5 |

It can be seen from the table that the fineness after long-term storage of the wettable powders containing the present hydrocarbon becomes significantly higher than that of the same wettable powders containing no present hydrocarbon, showing that the wettable powders containing the present hydrocarbon have excellent storage stability.

TEST EXAMPLE 2

Every wettable powder after 60 days' storage at 0° C. in Test Example 1 was measured for a suspensibility in the following condition.

250-ml glass stoppered measuring cylinders, each of which contained 250 ml of 3° hard water, were placed in a constant-temperature bath kept at 30° C., and 500 mg of each of the wettable powders was suspended in the cylinders. After 15 minutes, 25 ml of the water was sampled from the middle portion of the cylinder to obtain the suspensibility. The results are shown in Table 4 together with the test results on the same wettable powders as produced.

TABLE 4

| Wettable powder used for test | Suspensibility (%) | |
|---|---|---|
| | Before storage | After 60 days' storage at 0° C. |
| Example 2 | 93 | 92 |
| Comparative Example 1 | 93 | 64 |
| Example 4 | 94 | 94 |
| Comparative Example 2 | 91 | 69 |

It can be seen from the table that the suspensibility after long-term storage of the wettable powders containing the present hydrocarbon becomes significantly higher than that of the same wettable powders containing no present hydrocarbon, showing that the wettable powders containing the present hydrocarbon have excellent storage stability.

TEST EXAMPLE 3

The phytotoxicity test was carried out using the wettable powders produced in Example 1 and Comparative Example 3.

The test crop was chinese cabbage (var., Muso), and the dilution ratio of every wettable powder, a test sample, was 250. The test results are shown in Table 5 as a mean phytotoxicity level of three replications per plot.

TABLE 5

| Wettable powder used for test | Mean phytotoxicity level of three replications per plot |
|---|---|
| Example 1 | 0 |
| Comparative Example 3 | 0 |
| No treatment | 0 |

It can be seen from the table that the phytotoxicity to chinese cabbage of the wettable powder containing the present hydrocarbon is as low as that of the wettable powder containing no present hydrocarbon.

TEST EXAMPLE 4

100 Grams of each of the 10% dusts of a pesticide (a) produced in Example 8 and Comparative Example 4 was enclosed in an aluminum bag and stored at 0° C. for 60 days. Thereafter, 50 g of each of the dusts after 60 days' storage and the same dusts as produced was weighed and subjected to the wet sieving test with a 46 μsieve. The residue on the sieve was transferred to a Petri dish, dried on a water bath and weighed. The content of the residue on sieve of the test sample was calculated by weight percent. The results are shown in Table 6.

TABLE 6

| Dust used for test | Residue on sieve (%) | |
|---|---|---|
| | Before storage | After 60 days' storage at 0° C. |
| Example 8 | 0.5 | 0.6 |
| Comparative Example 4 | 1.9 | 3.8 |

It can be seen from the table that the fineness after long-term storage of the dust containing the present hydrocarbon becomes significantly higher than that of the same dust containing no present hydrocarbon, showing that the dust containing the present hydrocarbon has excellent storage stability.

TEST EXAMPLE 5

100 Grams of each of the 10% granules of a pesticide (e) produced in Example 9 and Comparative Example 5 was enclosed in an aluminum bag and stored by two ways, 5° C.×30 days and 0° C.×60 days. Thereafter, the granules after storage by two ways and the same granules as produced were tested for the spreading property in water, and the test results before and after storage were compared. The results are shown in Table 7.

TABLE 7

| Granule used for test | Difference in spreading property before and after storage | |
|---|---|---|
| | 5° C. × 30 days | 0° C. × 60 days |
| Example 9 | − | − |
| Comparative Example 5 | + | + |

−: No difference is observed visually.
+: Difference is observed visually.

It can be seen from the table that the spreading property of the granule containing the present hydrocarbon is kept stable even after long-term storage unlike the same granule containing no present hydrocarbon.

What is claimed is:

1. A dry pesticidal composition of a toxicant useful for crops having a melting point in a range of from 0° C. to 65° C. containing a hydrocarbon represented by the formula,

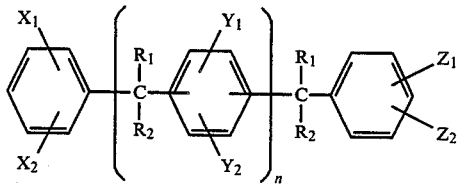

wherein $X_1$, $X_2$, $Y_1$, $Y_2$, $Z_1$ and $Z_2$, which may be the same or different, represent a hydrogen atom or an alkyl group having 2 or less carbon atoms, $R_1$ and $R_2$, which may be the same or different, represent a hydrogen atom or a methyl group, and n represents 0 or 1 and a pesticidally acceptable carrier.

2. A dry pesticidal composition according to claim 1, wherein the composition is a wettable powder.

3. A dry pesticidal composition according to claim 1, wherein the composition is a dust.

4. A dry pesticidal composition according to claim 1, wherein the composition is a granule.

5. A dry pesticidal composition according to claim 1, 2, 3 or 4, wherein the hydrocarbon is 1-phenyl-1-xylylethane or 1-phenyl-1-(ethylphenyl)ethane or a mixture of the both.

6. A dry pesticidal composition according to claim 1, 2, 3, or 4, wherein the toxicant is a pyrethroid compound.

7. A dry pesticidal composition according to claim 6, wherein the pyrethroid compound is at least one selected from the group consisting of fenvalerate, fenpropathrin, permethrin, cypermethrin and the isomers thereof.

8. A method for producing dry pesticidal compositions which comprises uniformly mixing a toxicant useful for crops having a melting point in a range of from 0° C. to 65° C. and a hydrocarbon represented by the formula,

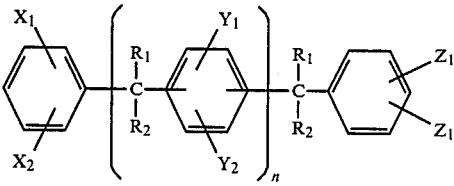

wherein $X_1$, $X_2$, $Y_1$, $Y_2$, $Z_1$ and $Z_2$, which may be the same or different, represent a hydrogen atom or an alkyl group having 2 or less carbon atoms, $R_1$ and $R_2$, which may be the same or different, represent a hydrogen atom or a methyl group, and n represents 0 and 1, and then mixing the resulting mixture with pesticidally acceptable carriers and if desired at least one additional ingredient selected from the group consisting of surface active agents, water-soluble polymers and auxiliaries.

9. A dry pesticidal composition according to claim 5, wherein the toxicant is a pyrethroid compound.

10. A dry pesticidal composition according to claim 9, wherein the pyrethroid compound is at least one selected from the group consisting of fenvalerate, fenpropathrin, permethrin, cypermethrin and the isomers thereof.

* * * * *